United States Patent
Farris et al.

[19]

[11] Patent Number: 5,928,237
[45] Date of Patent: *Jul. 27, 1999

[54] VARIABLE ANGLE SURGICAL CABLE CRIMP ASSEMBLY AND METHOD

[75] Inventors: Robert A. Farris, Memphis, Tenn.; M. Jeffrey Bonner, Southaven, Miss.

[73] Assignee: SDGI Holdings, Inc., Wilmington, Del.

[*] Notice: This patent is subject to a terminal disclaimer.

[21] Appl. No.: 08/934,794

[22] Filed: Sep. 22, 1997

Related U.S. Application Data

[60] Continuation of application No. 08/633,179, Apr. 16, 1996, abandoned, which is a division of application No. 08/219,763, Mar. 29, 1994, Pat. No. 5,569,253.

[51] Int. Cl.⁶ ..................................................... A61B 17/56
[52] U.S. Cl. .............................................. 606/74; 606/103
[58] Field of Search ................................. 606/60, 61, 74, 606/86, 103, 157, 151, 158, 232; 403/315; 24/16 R, 27, 28, 29, 115 L, 115 A, 115 R

[56] References Cited

U.S. PATENT DOCUMENTS

| | | |
|---|---|---|
| 2,509,272 | 5/1950 | Karnuth et al. . |
| 2,574,579 | 11/1951 | McCoy et al. . |
| 4,889,110 | 12/1989 | Galline et al. . |
| 4,966,600 | 10/1990 | Songer et al. . |
| 5,116,340 | 5/1992 | Songer et al. . |
| 5,395,374 | 3/1995 | Miller et al. . |

*Primary Examiner*—Guy V. Tucker
*Attorney, Agent, or Firm*—Woodard, Emhardt, Naughton, Moriarty & McNett

[57] ABSTRACT

A cable used in spinal surgery has one crimp of a two crimp assembly crimped to one end of it. The second crimp has a ball held in a socket of the first crimp. The other end of the cable is passed around the bone or bones and any necessary orthopedic spinal device and it is then passed through an aperture in the second crimp. The cable is then tensioned by application thereto of a tensioning tool with the tool applied to the cable and to an abutment face of the second crimp, whereupon the cable is tensioned, with the ball and socket arrangement enabling swiveling of the crimps with respect to each other, thus minimizing sharp bends in the cable. Then the second crimp portion receiving the cable portion in the aperture adjacent the tensioning tool is crimped onto that cable portion to complete the attachment. Then the tensioning tool is removed, and the free end of the cable is cut off at the abutment surface. Other embodiments include a bar with two swivel crimps captured therein and a cable passing from one of the crimps around some spinal processes and back into the other of the crimps. A further embodiment includes a bar with sets of concave seats for engaging but not capturing swivel crimps. A further embodiment includes a base factory-crimped to one end of the cable, and concave seats on opposite sides of the base for swivel mounting but not capturing a ball crimped to another portion of the cable.

3 Claims, 9 Drawing Sheets

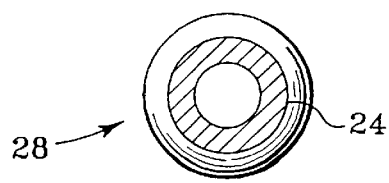
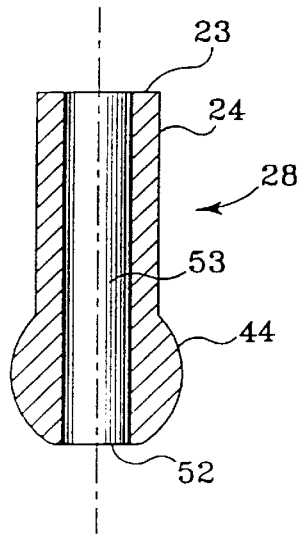
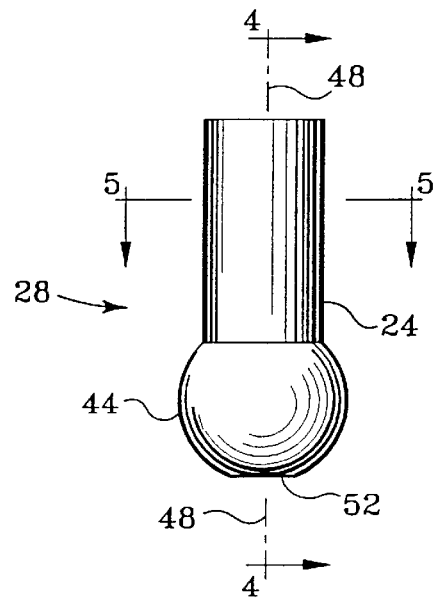
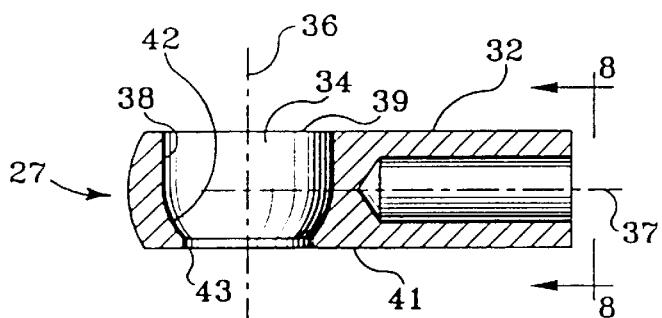
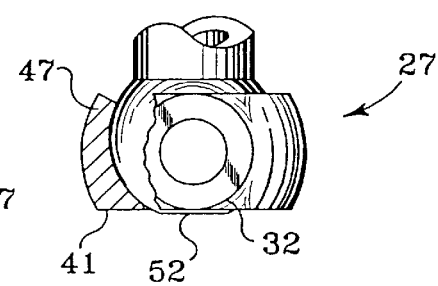
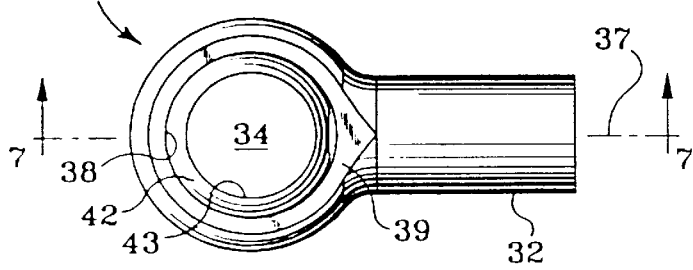

5,928,237

VARIABLE ANGLE SURGICAL CABLE CRIMP ASSEMBLY AND METHOD

This application is a continuation of application Ser. No. 08/633,179, filed Apr. 16, 1996, now abandoned, which is a divisonal of U.S. Ser. No. 08/219,763 filed on Mar. 29, 1994, which issued on Oct. 29, 1996 as U.S. Pat. No. 5,569,253.

BACKGROUND OF THE INVENTION

1. Field of the Invention

This invention relates generally to orthopedics and spinal surgery, and more particularly to a method and apparatus for securing surgical cable around bone.

2. Description of the Prior Art

Many ways and means have been developed for securing bone in place and for securing devices to bone. While single filament wires were used for many years in various types of surgical procedures, multi-filament cables have been used increasingly in recent years, particularly where strength and long-term reliability in a comparatively inaccessible site, are important. One example is shown in U.S. Pat. No. 4,889,110 issued Dec. 26, 1989 to Galline et al. In that example, an anchoring plate 11 has four bores therein receiving two crimping tubes and two crimping rings for holding multi-ply cables to secure a trochanter major to the femur. Another example of use of multi-filament cables is shown in U.S. Pat. Nos. 5,116,340 and 4,966,600 to Songer et al. The latter patent uses a loop 38 and a flanged tube crimp member 28 as in FIG. 1, or a stop member 94, bar 96 and a crimp member having a front flange 60 as in FIG. 6, to secure the cable. Because of the need to minimize space requirements for cabling, crimp members of the type shown in the Songer patents are small. As a result, they are difficult to handle, cannot be manipulated well with surgical gloves, and can be dropped easily. It is desirable to provide a system whereby a separate loose crimp is not needed, the crimp is reliably secured and securable to the cable, does not require tight bends or small loops in the cable, and which does not require cable-to-cable contact stress as in the cable passing through the small loop 38 in the FIG. 1 embodiment of the Songer patents.

SUMMARY OF THE INVENTION

Described briefly, according to a typical embodiment of the present invention, a surgical cable assembly has first and second crimps swivel-connected together. The first crimp has a body portion, and a barrel portion with an aperture therein. The second crimp has a ball portion, and a barrel portion with an aperture therein. The first crimp body portion has a socket therein for the ball portion of the second crimp. The ball portion and socket portions are shaped for swivel action together. One end of a surgical cable is received and factory crimped in the barrel aperture of the first crimp. At the surgical site, the other end of the cable is passed around the bone or bones and an orthopedic appliance or device if any is to be attached to the bones, and then it is passed through the aperture in the second crimp. Then the cable is tensioned by application of a tensioning tool to the cable and, directly or indirectly (through a provisional crimp), to an abutment face of the second crimp. When the desired final tension is established in the cable, the barrel of the second crimp is crimped onto the cable to complete the attachment. Then the tensioning tool is removed, and the free end of the cable is cut off at the abutment face of the second crimp.

Other embodiments include a base with two swivel crimps captured therein and a cable passing from one of the crimps around some spinal processes and back into the other of the crimps. A further embodiment includes a base with sets of concave seats for engaging but not capturing swivel crimps. A further embodiment includes a base factory-crimped to one end of the cable, and concave seats on opposite sides of the base for swivel mounting but not capturing a knob crimped to another portion of the cable.

BRIEF DESCRIPTION OF THE DRAWINGS

FIG. 3 is an enlarged elevational view of the ball-and-barrel part of the crimp assembly.

FIG. 4 is a section through the ball-and-barrel crimp taken at line 4—4 in FIG. 3 and viewed in the direction of the arrows.

FIG. 5 is a section therethrough taken at line 5—5 in FIG. 3 and viewed in the direction of the arrows.

FIG. 6 is a top plan view of the socket-and-barrel crimp.

FIG. 7 is a section therethrough taken at lines 7—7 in FIG. 6 and viewed in the direction of the arrows.

FIG. 8 is a view partially in section of the assembly of socket and ball viewed in the direction of arrows 8—8 in FIG. 7 but showing the socket swaged around the ball at the top to retain the ball in the socket.

DESCRIPTION OF THE PREFERRED EMBODIMENT

Figure 1:
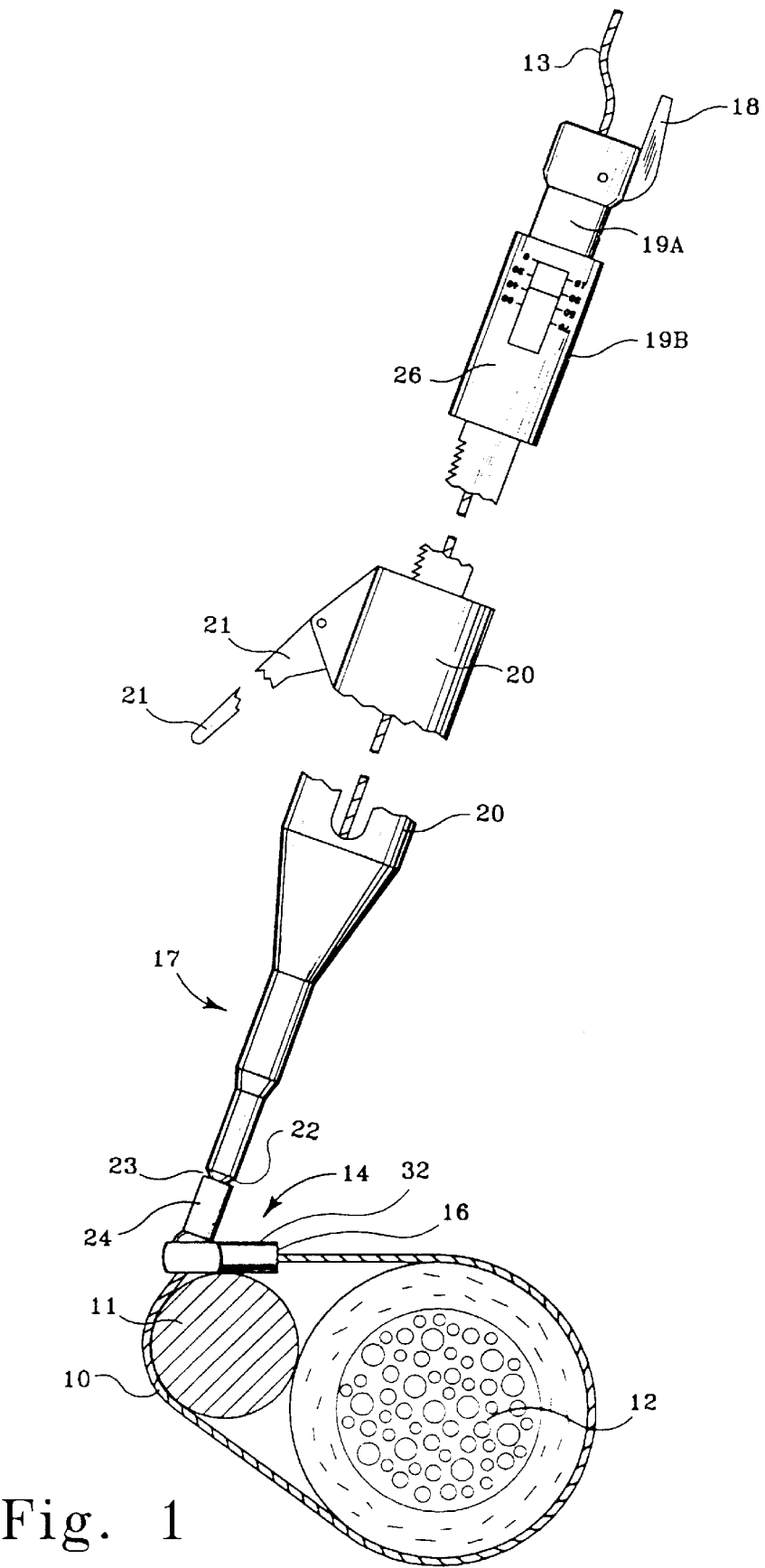
FIG. 1 is a schematic illustration of the application of a rod to a bone with the crimp assembly.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, and more particularly the example in FIG. 1, the goal is to secure cable 10 around a spinal rod 11 and bone 12, with the proper tension on the cable, and maintain it. For that purpose, the free end 13 of the cable is passed around the bone and rod while the crimp assembly 14 factory-crimped onto the cable at the other end 16 of the cable is held at a suitable location above the bone. Then the free end 13 is passed up through an aperture in the crimp assembly and then through the central passageway in a tensioning tool 17. Then a cable clamp 18 at the upper end of the tool 17 clamps a portion 19A of the tensioning tool onto the cable. Portion 19A telescopes within portion 19B which is secured to a bar which telescopes into the barrel 20 of the tensioning tool and, upon operation of the hand lever 21, portion 19B is ratcheted out of the barrel 20 whereupon the barrel tip 22 abuttingly engages the tool receiving abutment end 23 of an upper barrel portion 24 of the crimp assembly 14. Further ratcheting of the tool pulls the cable up through the an aperture in the upper barrel portion of the crimp assembly until the desired tension is reached, as indicated on the scale 26 on portion 19B of the tensioning tool in which portion 19A is restrained by a calibrated spring. Then a separate crimping tool (not shown) is applied to the barrel portion 24 of the crimp assembly and crimps it onto the cable portion extending through the aperture therein. Then the cable clamp 18 can be loosened, whereupon the tensioning tool can be removed from the cable and the cable is cut off at the abutment face 23, flush with face 23. The cable is secure to the bone. At this point, it should be mentioned that the tensioning tool is available from the assignee of the present invention, catalog number 825-210. Also, it is possible to use a provisional crimp (catalog number 825-200) between the end of the tensioning tool and the upper barrel portion of the crimp, if desired, during the tensioning procedure to maintain tension in the cable whereupon this tensioning tool can be removed to sequentially tighten multiple cables before final crimping. The crimping tool is assignee's catalog number 825-220. Other tensioning and crimping tools that provide proper tension and crimping capacity can be used with the cable assembly.

Figure 2:
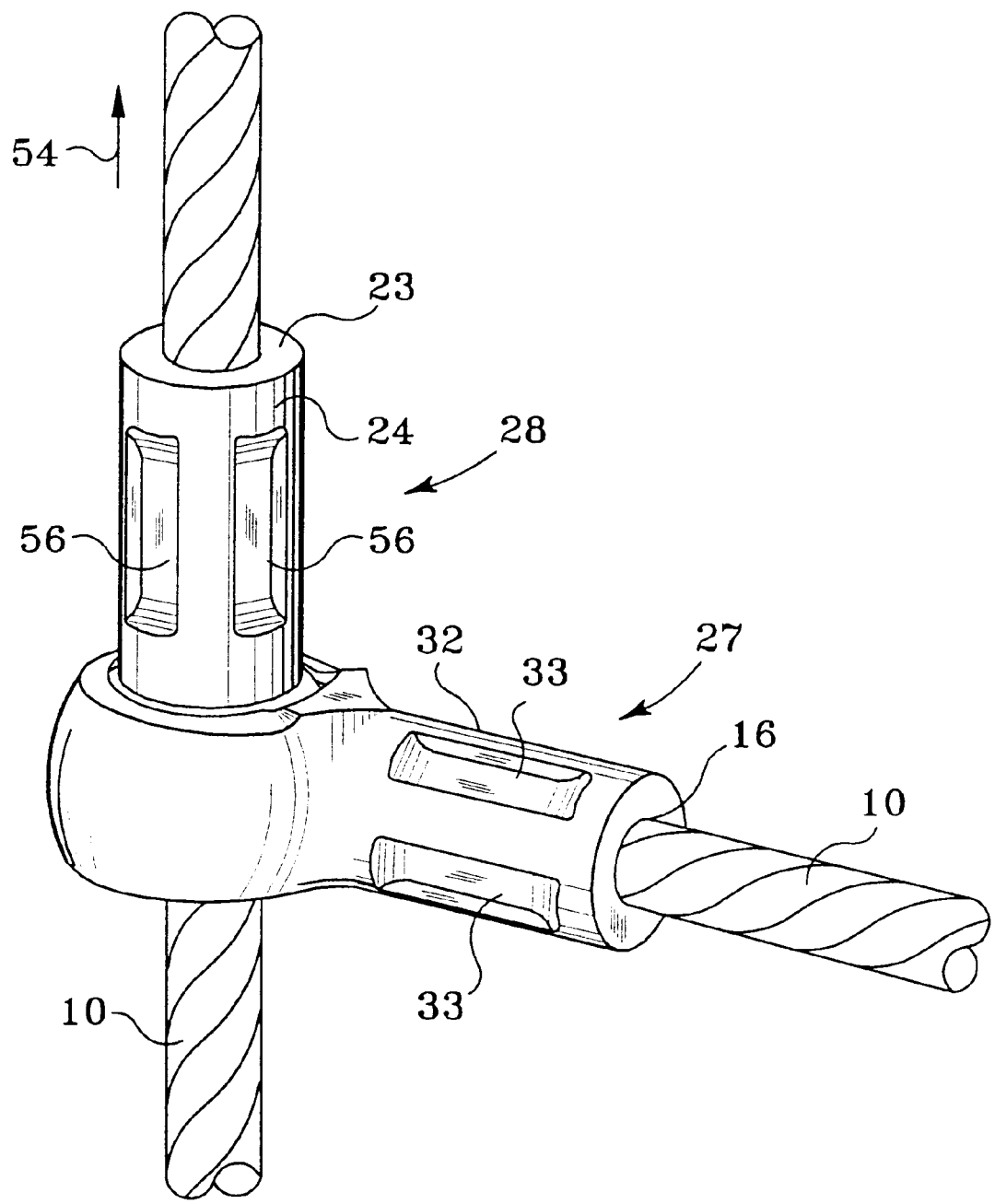
FIG. 2 is an enlarged fragmentary view showing the cable assembly with the new crimp assembly.

Referring more specifically now to FIG. 2, and for purposes of this application, the crimp assembly 14 is considered to be comprised of two crimps 27 and 28. One end portion 16 of the cable portion 10 of the cable assembly is snugly received in the longitudinally extending central aperture of the barrel portion 32 of crimp 27, and is secured therein by crimping at 33 in a die press at the factory. In addition to the aperture in which the cable end is crimped at 33, the crimp 27 also includes an aperture 34 (FIG. 7) extending through it on axis 36 of the cable receiving aperture. The aperture 34, prior to factory assembly of crimp 28 with crimp 27, has a cylindrical wall 38 extending down from the top 39 of the crimp. The wall of aperture 34 below cylindrical portion 38 has a spherical surface 42 which ends at the bottom opening 43 in the crimp.

Referring to FIG. 3, the second crimp 28 includes the ball portion 44 (which is preferably but not necessarily spherical) and barrel portion 24 projecting upward from it. The diameter of the ball portion 44 is slightly less than the diameter of the cylindrical surface 38 of the sphere of which spherical surface 42 is a part. After the spherical portion 44 of the crimp 28 is seated in the socket aperture 34 of crimp 27, the edge of opening 34 at the top surface 39 is swaged in as at 47 in FIG. 8, for example, to capture the ball in the socket, while permitting free swiveling action such that the axis 48 of the barrel of crimp 28 can move in a cone about the center of the spherical surface.

When the free end of the cable has been passed around the bone/bones or spinal rod or plate or other orthopedic device, if desired, it is then brought up through the lower end opening of the central aperture 53 in FIG. 4 in crimp 28 and out the upper end in the direction of arrow 54 in FIG. 2. It is then passed up through the tensioning tool as discussed above. The edge 52 at the intersection of the aperture 53 at the lower end of the spherical portion 44 of crimp 28 is "broken" to avoid a sharp edge. The aperture 53 is sized for a slip fit with the cable 10 so that, although the cable can be readily passed through the aperture for installing the cable around the bone or bones and rod or other orthopedic appliance, the crimp can be crimped onto the cable by a crimping tool such as mentioned above. Such crimping is indicated at 56 in FIG. 2, for example. The cable diameter is about 1.0 mm.

It should be understood, of course, that if it is desired to secure two bones within the loop of the cable, or one or more bones and spinal rods or other devices within the loop, that can be done in a similar manner.

As an example, in the stainless steel version, the crimp members and cable can be made from ASTM F-138 stainless steel, with the crimps annealed dead soft so that they can be easily crimped onto the cable. Alternatively, the cable can be made from ASTM F-136 Titanium alloy, and crimps can be commercially pure titanium (CP Ti) ASTM F-67, with the crimps annealed dead soft.

Figure 9:
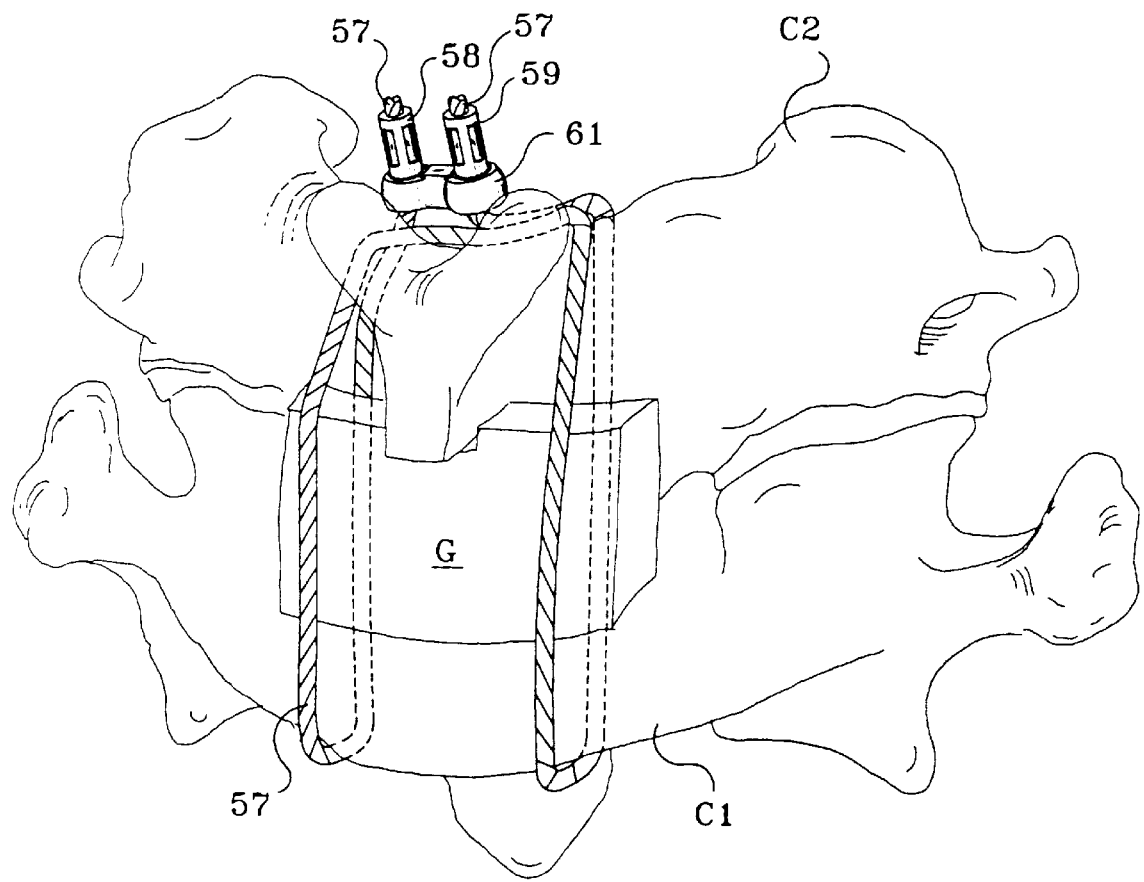
FIG. 9 is a pictoral view of another embodiment of the invention incorporating two ball-and-barrel crimps captured in a swivel socket bar with the cable wrapped from one of the crimps around spinal processes and graft and terminated in the other crimp.
Figure 10:
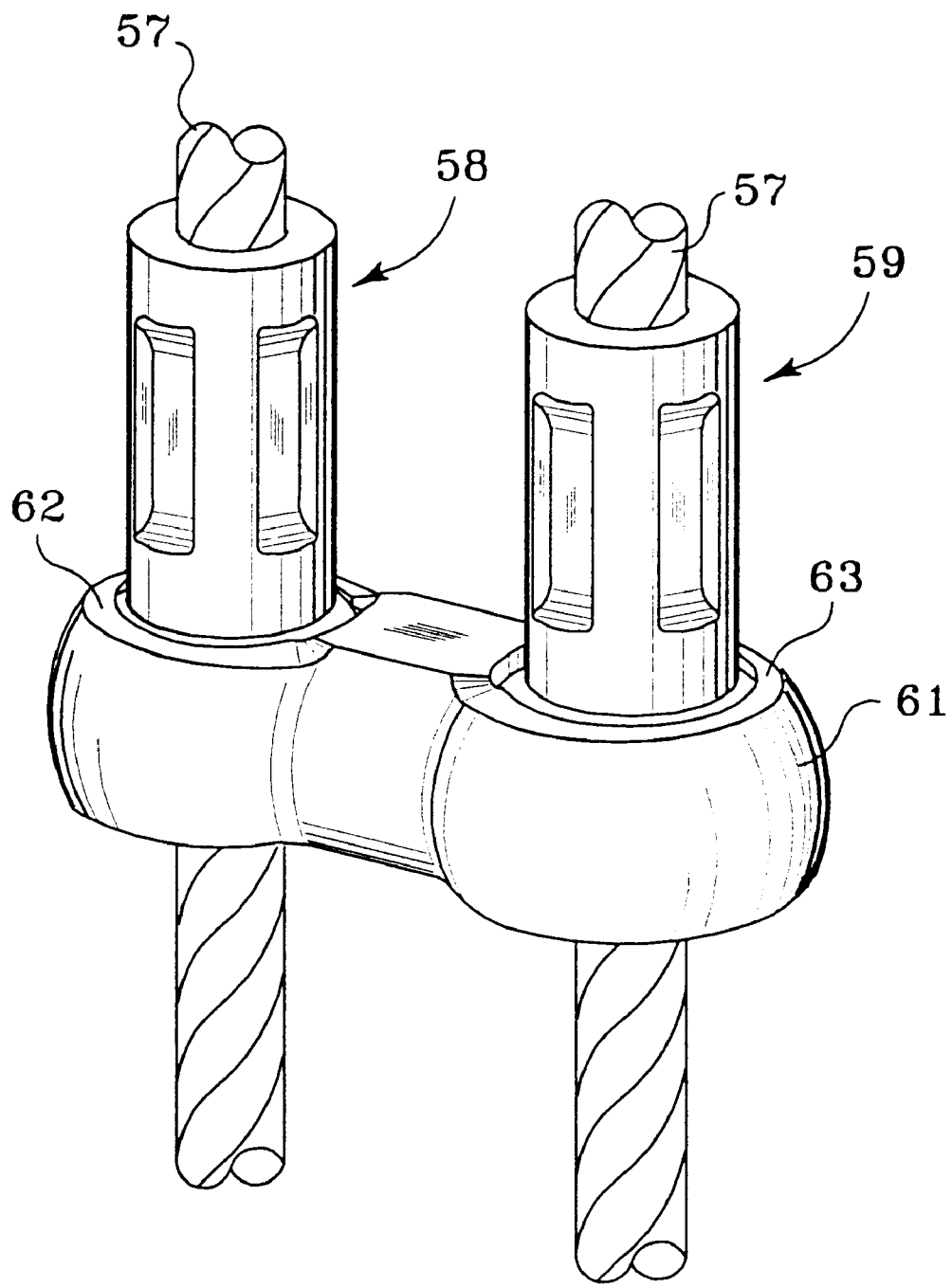
FIG. 10 is an enlarged pictoral view of the swivel crimp assembly.

Referring now to FIG. 9, vertebral bodies C1 and C2 together with bone graft G, are shown inverted for convenience of the reader in comparing various embodiments of the invention. The bone graft is held in place by cable 57 around the processus of C1 and C2. This cable passes down through the ball-and-barrel crimp 58, around the processus of C1 and C2 and terminates through the ball-and-barrel crimp 59. The crimps 58 and 59 are identical and the ball of each is captured in one of the two sockets in the bar 61 in the same manner as the ball 44 of the ball-and-barrel crimp 28 of the earlier embodiment is captured in the socket-and-barrel crimp 27 as shown in FIG. 8. For the tightening of the cable and crimping, the same tensioner as described above with reference to the first embodiment, with or without the provisional crimps as mentioned above, can be used. The fact that the ball portions are swaged into the sockets at 62 and 63 in the bar 61, as shown in FIG. 10, makes it particularly easy to manage this assembly since the crimps are captured in the bar at all times during use. In this embodiment, depending upon the technique shown, the practitioner is likely to have a substantial length of cable projecting up through each of the crimps 58 and 59 during the procedure, particularly if it is desirable to use the tensioner alternately on the two cables using the provisional crimps.

Figure 11:
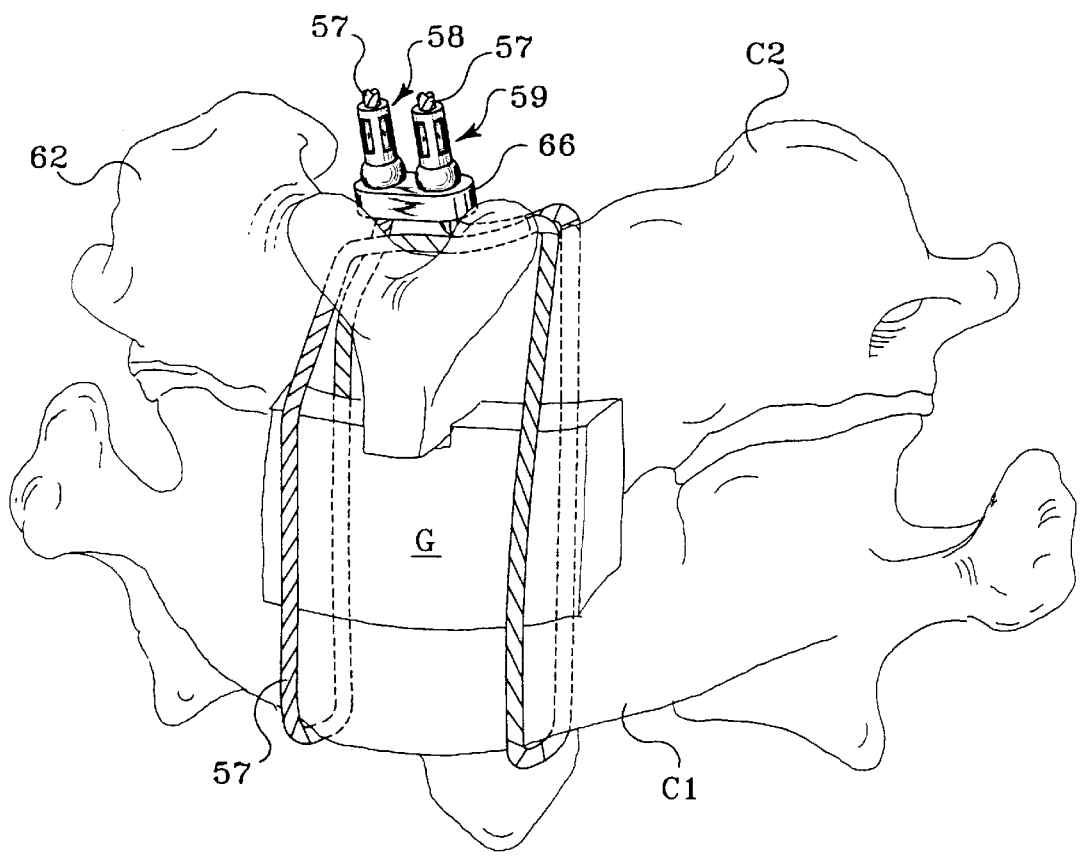
FIG. 11 is a view similar to FIG. 9 but showing two ball-and-barrel crimps not captured-in, but centered in concave seats in a base.

Referring now to FIG. 11, the arrangement is the same as in FIG. 9, except that the support base 66 for the two ball-and-barrel crimps 58 and 59 is different. As shown more specifically in FIGS. 12 and 13, the ball portion 68 and ball portion 69 of the crimps rest in hemispherical seats 71 and 72 of the bar 66. Consequently, they are not captured in the base, in contrast to the embodiment previously described. Also, in this particular embodiment, the bar has hemispherical cavities 73 and 74 in the-underside thereof. They are identical to 71 and 72 whereby the bar is symmetrical and can be used with either face up.

Figure 12:
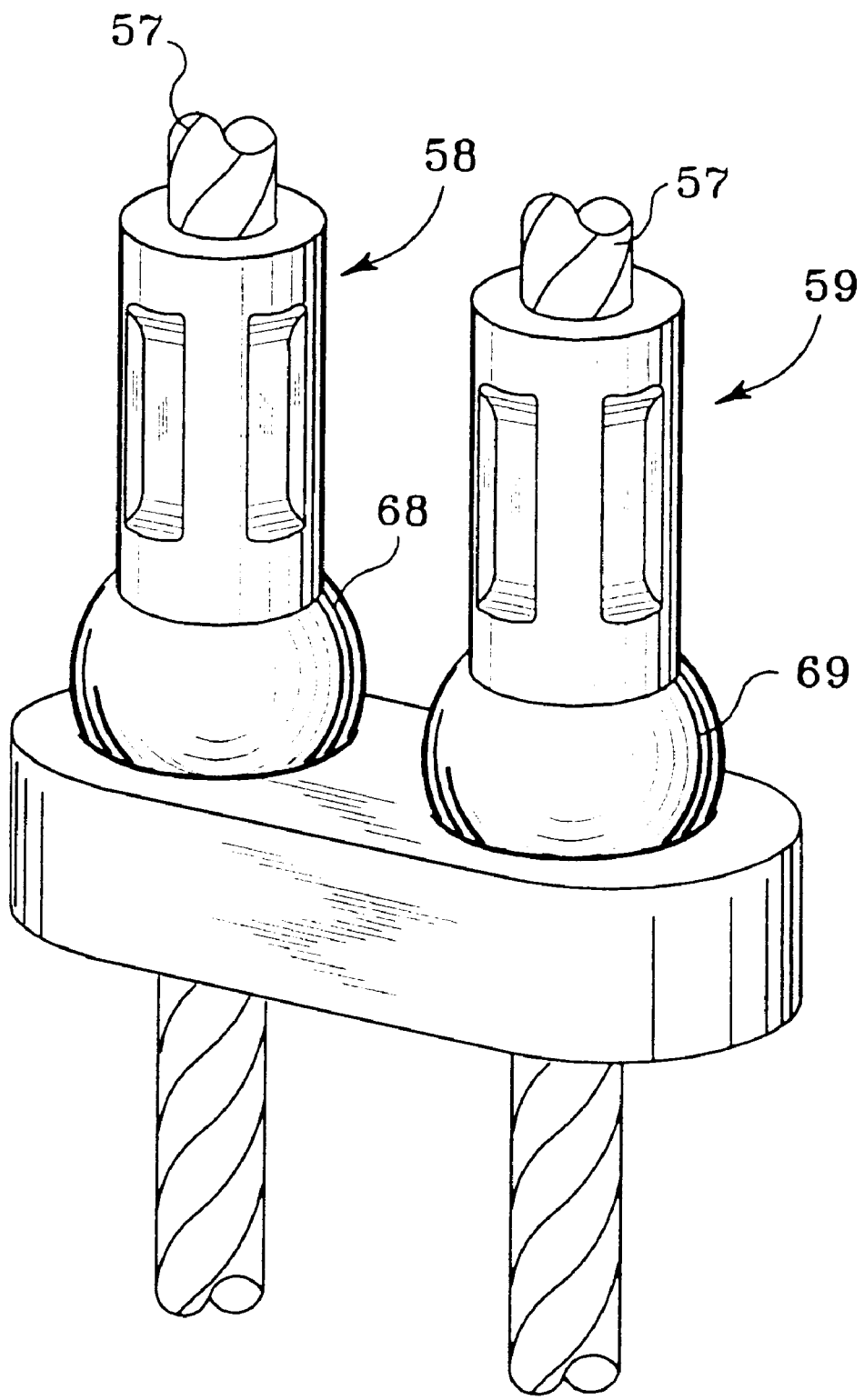
FIG. 12 is an enlarged pictoral view of the crimp assembly of FIG. 11.
Figure 13:
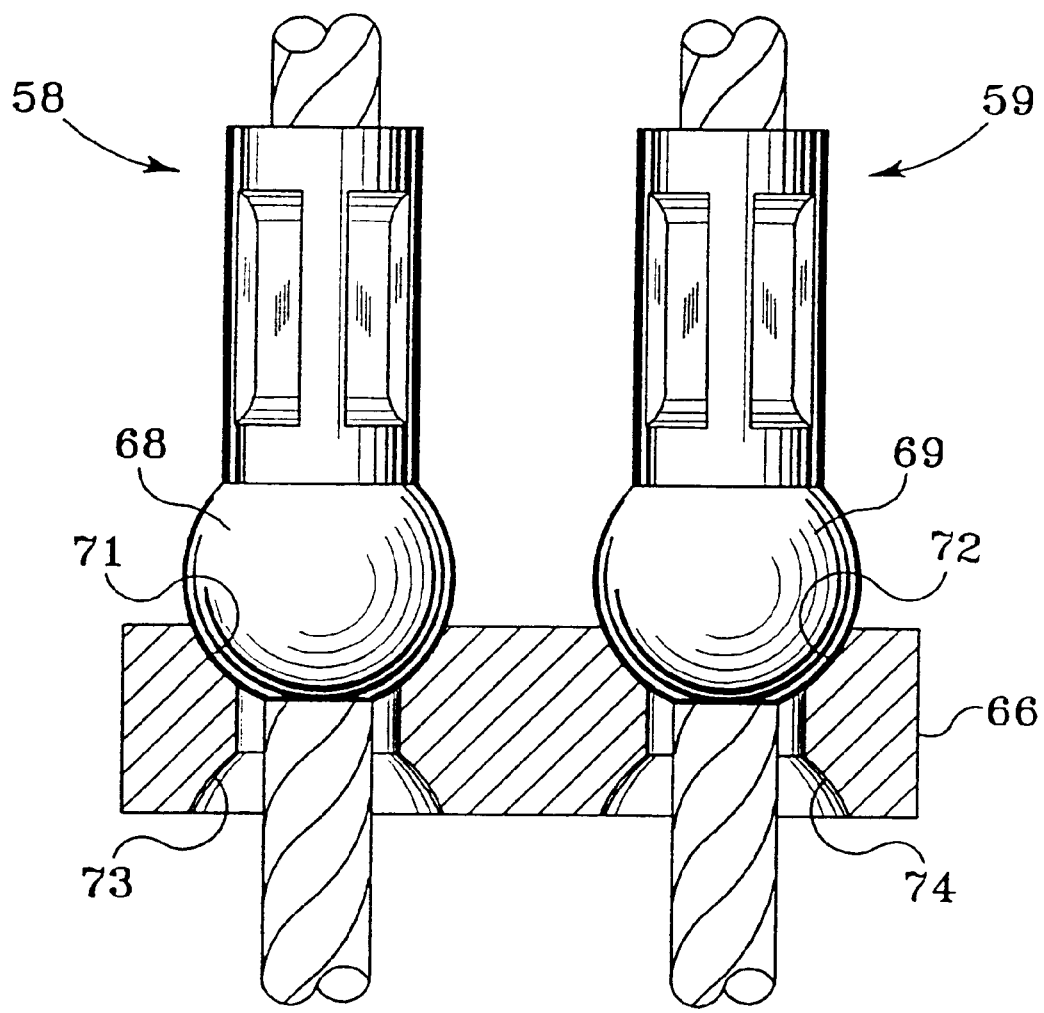
FIG. 13 is a sectional view therethrough.
Figure 14:
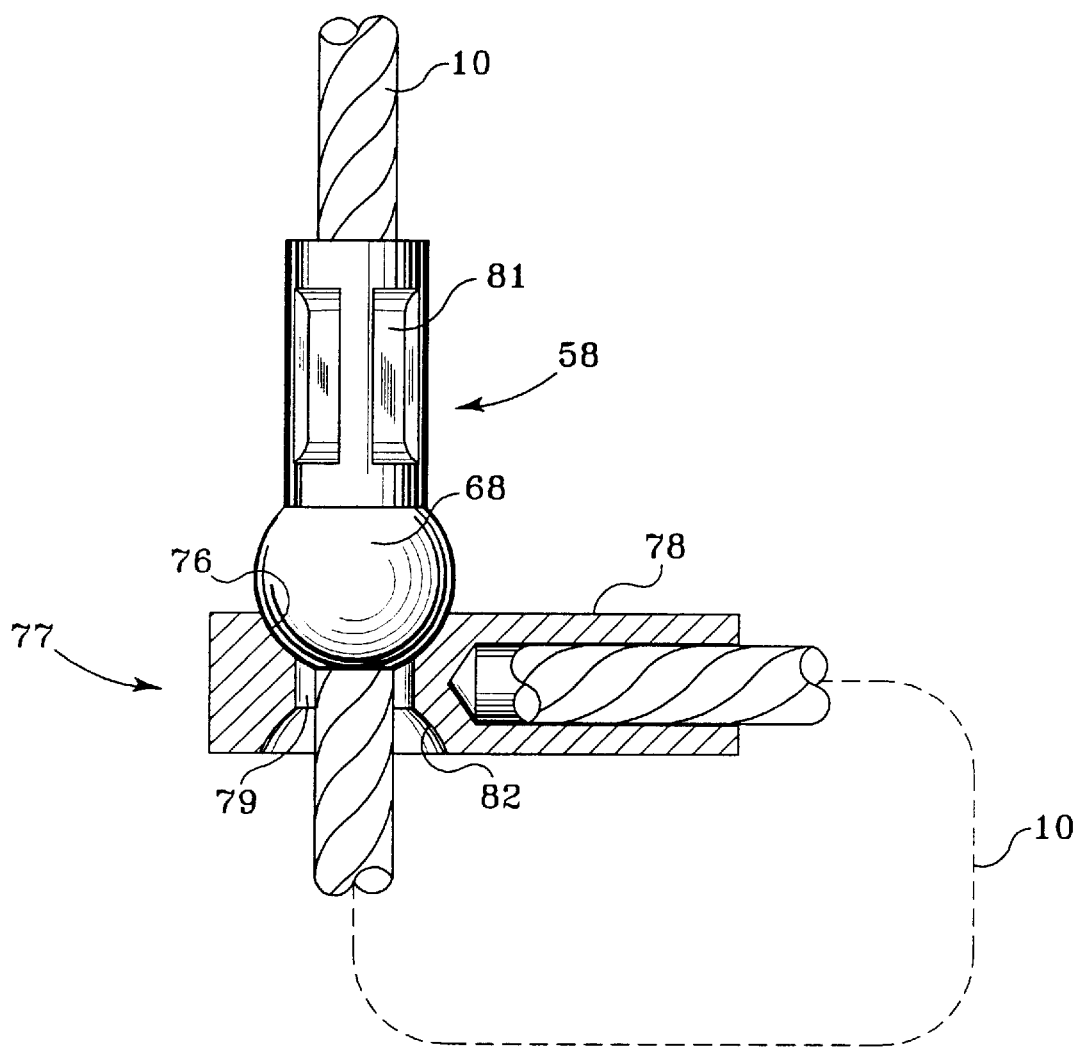
FIG. 14 is a sectional view through a ball-and-barrel crimp seated in a concave base factory crimped to one end of a cable, with the other end portion of the cable passing up through the crimp.

Referring now to FIG. 14, the assembly is similar to that of FIG. 2 and can be used in the same manner as FIG. 1 but, as in FIGS. 11 through 13, the barrel-and-ball crimp 58 has the ball thereof merely bearing on the hemispherical seat 76 of the base plate 77. One end of the cable 10 is factory crimped at 78 into the barrel portion of the base 77, while the other end is passed around the bone and rod (not shown in FIG. 14) in a manner similar to that in FIG. 1, and up through the seat aperture 79 in the base crimp 77 and up through the crimp 58 where, after tensioning as described to the FIG. 1 embodiment, it is crimped as at 81. In this embodiment also the top and bottom of the base crimp 77 are identical, the seats 76 and 82 are identical, so the crimp 58 can be used at either face of the base crimp 77.

The materials for the additional embodiments of the invention described with reference to FIGS. 9 through 14 can be the same as described above with reference to the FIG. 1 through 8 embodiments. Also it should be understood that, if desired for certain types of cabling procedures, the crimp assembly of FIG. 2, together with the cable crimped in the socket in barrel portion 32, can have a leader with one end welded onto the other end of the cable. The other end of the leader is welded to one end of a second cable which has at its other end, another crimp assembly such as 14 with the barrel portion such as 32 crimped to the opposite end of the second cable. After forming the leader into a U-shape and feeding the cable assembly around the appropriate spinal processus and any support accessories, the leader can be severed at the middle, and the cables then are fed up through the ball-and-barrel crimps and crimped thereto in the manner as described above with reference to FIG. 1. Also, a single length of cable can be provided with a leader at one end and a leader at the other end to facilitate use of the cable with crimp assemblies such as shown in FIGS. 9 through 13.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical cable assembly comprising:

a base;

a first crimp having a crimpable portion with an aperture therein;

a second crimp having a crimpable portion with an aperture therein; and a surgical cable having one portion received and crimped in the aperture of the first crimp;

the crimps having bearings engaging the base and enabling change of attitude of the second crimp relative to the first crimp;

the cable extending from the portion crimped in the aperture of the first crimp, through the bearing of the first crimp and through the base in one direction, and then back through the base in the opposite direction and through the bearing of the second crimp and into the aperture of the second crimp where a second portion of the cable is crimped.

2. The assembly of claim 1 and wherein:

the crimps have barrel portions outside the base.

3. A surgical cable assembly comprising:

a base;

a first barrel having a cable receiving portion with an aperture therein;

a second barrel having a cable receiving portion with an aperture therein; and a surgical cable having one portion engaged in the aperture of the first barrel;

the barrels having bearings engaging the base and enabling change of attitude of the second barrel relative to the first barrel;

the cable extending from the portion engaged in the aperture of the first barrel, through the bearing of the first barrel and through the base in one direction, and then back through the base in the opposite direction and through the bearing of the second barrel into the aperture of the second barrel where a second portion of the cable is engaged.

* * * * *